United States Patent [19]

Godtfredsen

[11] Patent Number: 4,554,160
[45] Date of Patent: Nov. 19, 1985

[54] PENICILLIN ESTERS, SALTS THEREOF AND METHODS FOR THEIR PREPARATION

[75] Inventor: Wagn O. Godtfredsen, Vaerløse, Denmark

[73] Assignee: Lovens Kemiske Fabrik Produktionsaktieselskab, Denmark

[21] Appl. No.: 554,423

[22] Filed: Mar. 3, 1975

Related U.S. Application Data

[62] Division of Ser. No. 243,855, Apr. 13, 1972, Pat. No. 3,869,449.

[51] Int. Cl.[4] ............................................. A61K 35/00
[52] U.S. Cl. ..................................................... 424/114
[58] Field of Search ........................................ 424/114

Primary Examiner—Jerome D. Goldberg
Attorney, Agent, or Firm—Jon S. Saxe; Bernard S. Leon

[57] ABSTRACT

The invention relates to a new series of penicillin esters and salts thereof, to methods of their preparation and to intermediates in the production of the esters of the general formula

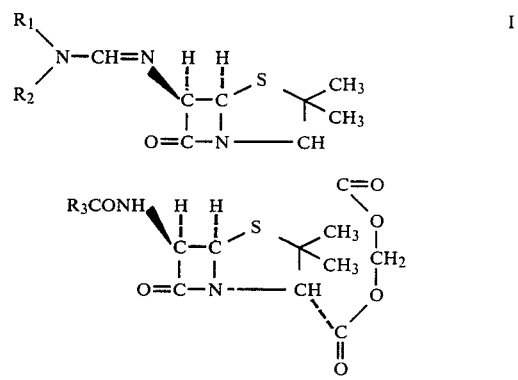

in which $R_1$ and $R_2$ represent an alkyl radical having from 1 to 6 carbon atoms, a cycloalkyl or cycloalkylalkyl radical the cycloalkyl part having from 3 to 10 carbon atoms, or $R_1$ and $R_2$ together with the nitrogen atom represent a heterocyclic ring with from 4 to 8 carbon atoms; $R_3$ represents radicals known from natural, biosynthetic, and semisynthetic penicillins; and pharmaceutically acceptable salts thereof.

The new compounds are efficiently absorbed from the gastrointestinal tract and after the absorption they are rapidly transformed into the corresponding free penicillins and amidinopenicillanic acids, whereby a broad-spectrum infection can be combated.

1 Claim, No Drawings

PENICILLIN ESTERS, SALTS THEREOF AND METHODS FOR THEIR PREPARATION

This is a division of U.S. patent application, Ser. No. 243,855, filed Apr. 13, 1972, now U.S. Pat. No. 3,869,449.

This invention relates to a new series of penicillin esters, to salts thereof and to methods of their preparation.

The new penicillin esters have the general formula I:

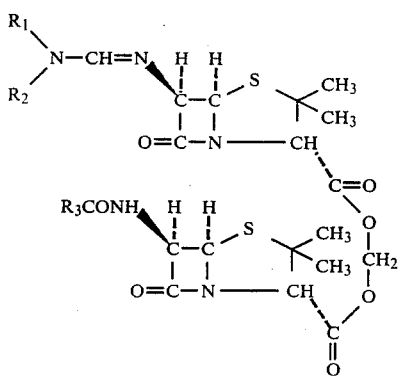

in which $R_1$ and $R_2$ represent an alkyl radical having from 1 to 6 carbon atoms, a cycloalkyl or cycloalkylalkyl radical the cycloalkyl part having from 3 to 10 carbon atoms, or $R_1$ and $R_2$ together with the nitrogen atom represent a heterocyclic ring with from 4 to 8 carbon atoms. In particular, $R_1$ and $R_2$ which may be the same or different represent e.g. a methyl, ethyl, propyl, isopropyl, n-butyl, sec.butyl, tert.butyl, one of the isomeric pentyl or hexyl radical, a cyclopentyl, cyclohexyl, 1-adamantyl, 1-bicyclo(2.2.2)octyl, cyclopentyl and cyclohexenyl, cyclopentylmethyl, cyclohexylmethyl, cyclopentenylethyl, cyclohexenylmethyl etc., or $R_1$ and $R_2$ when taken together with the nitrogen atom represent heterocyclic radicals having from 4 to 8 carbon atoms and optionally containing other hetero atoms in the ring, such as S, O or N, forming more or less hydrogenated ring systems e.g. piperidyl, morpholinyl, hexahydro-1H-azepin-1-yl, or hexahydro-1(2H)-azocinnyl. The radicals $R_1$ and $R_2$ may be further substituted with halogen atoms, an alkyl, hydroxy, alkoxy, alkylthio group, an acyl group, a carboxy, carbalkoxy, carbamyl, carbamido, cyano or sulfonyl group, an amino- or substituted amino group.

$R_3$ represents radicals known from natural, biosynthetic and semisynthetic penicillins. Such radicals are e.g. benzyl, phenoxymethyl, 2,6-dimethoxyphenyl, α-azidobenzyl, α-aminobenzyl, α-carboxybenzyl, α-phenoxyethyl, α-phenoxypropyl, 3-phenyl-5-methyl-4-isoxazolyl, 3-(2-chlorophenyl)-5-methyl-4-isoxazolyl, 3-(2,6-dichlorophenyl)-5-methyl-4-isoxazolyl, 3-(2-chloro-6-fluorophenyl)-5-methyl-4-isoxazolyl, 2-ethoxy-1-naphtyl, 2-thienylmethyl, 3-thienylmethyl and α-(3-guanyl-1-ureido)-benzyl.

The salts of the new compounds are salts with inorganic or organic pharmaceutically acceptable acids such as hydrochloric acid, hydrobromic acid, sulfuric acid, phosphoric acid, tartaric acid, citric acid, fumaric acid, maleic acid, p-(N,N-dipropylsulfamyl)-benzoic acid and the like acids.

When $R_1$, $R_2$ or $R_3$ contain asymmetric carbon atoms the compounds of the invention will exist in different diastereoisomeric forms and the invention comprises all of these forms as well as mixtures thereof. The form in which the compounds are obtained depends on which enantiomer of the starting materials and which method is used to make the compounds. The mixtures of the diastereoisomers may be separated by fractional crystallization or other known methods.

In contrast to the amidinopenicillanic acids and some of the free penicillins the compounds of the invention are efficiently absorbed from the gastrointestinal tract and after the absorption they are rapidly transformed into the corresponding free penicillins and amidinopenicillanic acids, either spontaneously or under the influence of enzymes present in the body.

By oral administration the new esters of the invention give rise to high concentrations of the corresponding free penicillins and amidinopenicillanic acids in blood and tissues due to efficient absorption combined with rapid hydrolysis in the organism, whereby a broad-spectrum infection can be combated, due to the fact that the amidinopenicillins possess strong antibacterial effect especially on gram-negative bacteria.

It has also been found that by the simultaneous high concentrations of these two types of antibiotics a synergistic effect is obtained (for instance by administration of the compound of formula I in which $R_1R_2N-$ stands for a hexamethyleneimine radical and $R_3$ is benzyl).

The compounds of formula (I) are well tolerated compounds which are administered in clinical practice either as such or, preferably, in the form of one of their salts mixed with carriers and/or auxiliary agents and in any suitable form of pharmaceutical presentation for oral use, such as tablets, pills or dragees, or can be filled in medical containers such as capsules, or as far as suspensions are concerned, filled into bottles. Pharmaceutical organic or inorganic, solid or liquid carriers suitable for oral administration can be used to make up the composition. Gelatine, lactose, starch, magnesium stearate, talc, vegetable and animal fats and oils, gum, polyalkylene glycol, or other known carriers for medicaments are all suitable as carriers. The preferred salt of the esters is the hydrochloride, but salts with other inorganic or organic acids may be used as mentioned above. Furthermore, the compositions may contain other pharmaceutically active components which can appropriately be administered together with the ester in the treatment of infectious diseases.

The compounds of the invention can be prepared by several methods. In the first method a salt of a penicillin of the general formula II is reacted with a compound of the general formula III

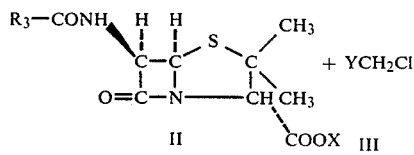

in which formulae $R_3$ is as defined above, X is a cation such as a potassium, sodium, ammonium or trialkylammonium ion and Y represents a bromine atom, an iodine atom, an alkylsulphonyloxy group or an arylsulphonyloxy group, preferably in an inert organic solvent, e.g. dimethylformamide or acetone, and at room temperature or at slightly elevated temperatures, whereby a compound of the general formula IV, in which $R_3$ is as defined above, is obtained:

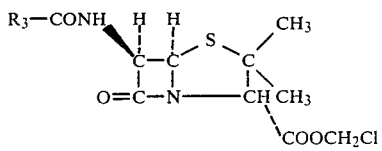

The compounds of formula IV are then reacted with a salt of a compound of the general formula V:

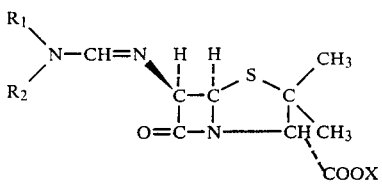

in which $R_1$, $R_2$ and X are as defined above, at room temperature or at slightly elevated temperatures, whereby a compound of formula I is obtained.

The compounds of formula V are disclosed in the following section, or perhaps rather subsection, designated Section A. It will be noted that the section refers to the subject matter with which it deals, including the compounds of the above formula V and related compounds and their method of making, as "the invention" and "this invention", which in this case is a convenient term of reference, not intended to indicate that the subject matter of this Section A is an invention that anyone is seeking to patent in this present application. To distinguish the various formulae, examples and R numbers, etc., in Section A from those in the rest of the specification, the ones in Section A are being given the suffix a. It will be noted that formula Ia, when $R_{4a}$ makes a salt of the hydroxide and $R_{3a}$ is hydrogen, corresponds to formula V except for the greater breadth of $R_{1a}$ and $R_{2a}$ as compared to $R_1$ and $R_2$. The particular interrelation between formula IIa and formula IX will also be noted.

SECTION A DEVOTED TO THE INTERMEDIATES OF FORMULA V AND THEIR METHOD OF MAKING

This invention relates to once unknown derivatives of 6-aminopenicillanic acid, to pharmaceutically acceptable salts thereof, and to methods for the production of these same compounds.

The compounds of the invention have the general formula:

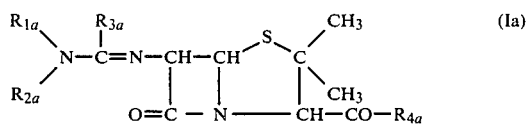

in which $R_{1a}$ and $R_{2a}$ represent the same or different substituents and each represents an aliphatic hydrocarbon radical, an aralkyl radical, a cycloalkyl radical, a cycloalkyl-alkyl radical, a heterocyclically substituted alkyl radical; $R_{1a}$ and $R_{2a}$ together with the nitrogen atom represent a ring system; $R_{1a}$ and $R_{3a}$ together with the N—C atoms represent a ring system; $R_{3a}$ can furthermore be hydrogen or have the same meaning as $R_{1a}$; $R_{4a}$ represents a hydroxyl group, an esterified hydroxyl group, or a substituted or unsubstituted amino group radical.

More particularly, $R_{1a}$, $R_{2a}$ and $R_{3a}$ represent an aliphatic hydrocarbon radical in which the carbon chain can be straight or branched, saturated or unsaturated, and may be interrupted by an oxygen or a sulphur atom, such as methyl, ethyl, propyl, isopropyl, butyl, sec.butyl, tert. butyl, pentyl, hexyl, dodecyl, allyl, butenyl, pentenyl, propargyl, methoxyethyl, ethoxyethyl, methylthioethyl and the like; an aralkyl radical, such as mono- or bicyclic aralkyl radical, e.g., benzyl, phenylethyl, 1- or 2-naphthylmethyl; a cycloalkyl or cycloalkyl-alkyl radical, having from 3 to 10 ring members and being saturated or having one or two double bonds, such as cyclopentyl, cyclohexyl, 1-adamantyl, 1-bicyclo(2.2.2)octyl, cyclopentyl and cyclohexenyl; a heterocyclically substituted alkyl radical in which the heterocyclic part can have from 5 to 10 atoms in the ring and can contain further hetero atoms, for example, oxygen, sulphur, or nitrogen, such as pyridyl, pyrazinyl, pyrimidyl, pyrrolidyl, piperidyl, hexamethyleneimine, heptamethyleneimine, morpholinyl, thiazinyl, furyl, thienylquinolyl, in all of which the hetero atoms may be placed in any of the available positions; $R_{1a}$ and $R_{2a}$ together with the nitrogen atom, or $R_{1a}$ and $R_{3a}$ together with the N—C atoms represent heterocylic ring systems having from 5 to 10 atoms and optionally containing other hetero atoms in the ring, such as S, O, or N, forming more or less hydrogenated ring systems e.g. piperidyl, morpholinyl, hexa- or heptamethyleneimine. All the radicals $R_{1a}$, $R_{2a}$ and $R_{3a}$ may be further substituted with halogen atoms, alkyl groups or alkoxy groups.

More particularly, $R_{4a}$ represents a hydroxyl group, a substituted hydroxyl group $OR_{5a}$ in which $R_{5a}$ stands for an alkyl radical, aryl radical, aralkyl radical, an alkyl radical substituted with alkoxy, alkanoyl, aroyl, cyano, or a carbalkoxy group, e.g. methyl, ethyl, phenyl, benzyl, methoxymethyl, acetonyl, phenacyl, cyanomethyl, carbethoxymethyl, or dicarbethoxymethyl and the like; $R_{5a}$ further represents an acyloxymethyl radical the acyl part of which being an aliphatic, alicyclic, aromatic, ar-aliphatic or heterocyclic radical. such as acetyl, propionyl, butyryl, pivaloyl, cyclohexylacetyl, benzoyl, phenylacetal, picolinyl, nicotinyl, furylacetyl, thienylacetyl etc., or $R_{4a}$ can represent an $NR_{6a}R_{7a}$ radical, in which $R_{6a}$ and $R_{7a}$ are hydrogen, or have the same meanings as defined for $R_{1a}$, or together with the nitrogen atom form a ring in the same manner as defined for $R_{1a}R_{2a}N$.

The componds of formula Ia may be isolated as such or in the form of a salt with a pharmaceutically acceptable acid, such as hydrochloric acid, phosphoric acid, nitric acid, acetic acid, propionic acid, citric acid, tartaric acid, maleic acid, etc. When $R_{4a}$ stands for a hydroxyl group the compounds of formula Ia may be isolated as the acid and as a salt thereof, preferably the alkali metal salts and the ammonium salts.

The invention comprises all possible isomeric forms of the compounds of formula Ia.

The compounds of the invention possess strong antibacterial effect especially on gram-negative bacteria and the oral toxicity is extremely low. This effect is quite unexpected, since hitherto only derivatives of 6-aminopenicillanic acid substituted in the 6-position with an acyl group have shown an anti-bacterial effect. The effect on penicillin-sensitive, gram-positive bacteria is less than that of benzylpenicillin and α-aminobenzylpenicillin, whereas the effect on gram-negative bacteria, e.g. coli and salmonella species, is on a many times higher level than that of penicillins. Preliminary in vitro experiments indicate activities up to 700 times the activity of benzylpenicillin and up to 50 times the activity of α-amino-benzylpenicillin on coli bacteria and for salmonella bacteria the corresponding figures are 50 times and 10 times, respectively. For certain pharmaceutical purposes it will be advantageous to use the free acids or their salts, whereas it for other purposes will be more favourable to use the easily hydrolyzable esters, which in the organism will be enzymatically hydrolyzed to the corresponding free acids. In other cases the less hydrolyzable esters or amides will be preferred in order to obtain particular ratio of distribution in the body.

The invention also comprises methods for the preparation of the above described compounds. In a preferred method the compounds of formula Ia are prepared in two steps from amides of the general formula II:

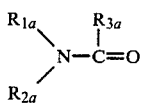

(IIa)

in which $R_{Ia}$, $R_{2a}$ and $R_{3a}$ have the meanings defined above. These starting materials are known or may be prepared by methods known from generally used textbooks. By a generally known reaction these amides can be transferred into the corresponding amide halides, some of which are also known compounds, having the formula IIIa.

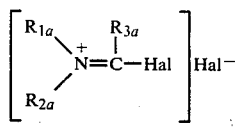

(IIIa)

in which $R_{1a}$, $R_{2a}$ and $R_{3a}$ have the above given meaning and Hal stands for halogen, preferably chlorine or bromine. All well-known halogenating agents can be used, but it is preferable to use halogenating agents, which throughout the course of the reaction form gaseous by-products, such as phosgene or oxalyl chloride or bromide but also others, e.g. thionyl halides, may be used. The reaction can be performed in inert, dry, organic solvents, e.g. ether or toluene, in which the amide halide in most cases will be insoluble and from which it can be isolated by filtration after the reaction is completed. The compounds of formula III are hygroscopic and rather unstable and are therefore preferably used in the next step without purification.

In the next step the amide halide is reacted with a compound of the general formula IVa, yielding the compounds of the invention:

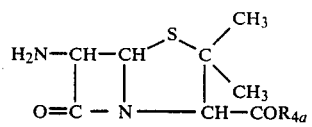

(IVa)

in which $R_{4a}$ has the meaning defined above. The reaction is performed at low temperature and in inert organic solvents, which are dry and free from traces of alcohols, preferably chloroform, in which the reaction components are soluble, but solvents in which the amide halide is insoluble, e.g. ether, may be used as well. The reaction is performed under cooling and in the presence of at least one equivalent of a tertiary amine. In the case where one equivalent of the tertiary amine is used, the reaction product will be isolated as the hydro halide, whereas the free amidines will be obtained when two or more equivalents of the tertiary amine are used.

The reaction time depends on the reactants, the temperature and the solvents used in the process. In the case where $R_{4a}$ stands for a hydroxyl group, it is preferred to protect the carboxyl group with a trimethylsilyl radical which, after the reaction easily can be split off again. The preparation of the trimethylsilyl ester of 6-aminopenicillanic acid is known from the literature. The trimethylsilylester of the amidine is preferably cleaved by a hydrolysis or an alcoholysis under mild conditions.

The reaction products of formula Ia can be purified and isolated in usual manner and may be obtained either in free state or in the form of a salt. The free acid can also be obtained from some of the esters by an enzymatic hydrolysis or a mild hydrogenolysis, and if the free acid is the reaction product the esters and the amides can be prepared therefrom by methods known from the literature.

The compounds of formula IVa are partly known compounds and may be prepared by esterification or amidation of 6-aminopenicillanic acid or a protected 6-aminopenicillanic acid, such as the 6-trityl derivative thereof. The trityl group may be split off after the reaction under conditions not affecting the lactam ring. They can also be prepared by esterification or amidation of the generally industrially used penicillins, whereafter the acyl side chain can be split off chemically or enzymatically under such conditions that the ester group or the amide group is not affected.

The compounds of formula (Ia) are well tolerated compounds which may preferably be administered orally either as such or, in form of one of their salts, and may be mixed up with a solid carrier and/or auxiliary agents. In such compositions, the proportion of therapeutically active material to carrier substance and auxiliary agent can vary between 1% and 95%. The compositions can either be worked up to pharmaceutical forms of presentation such as tablets, pills or dragees, or can be filled in medical containers such as capsules, or as far as mixtures are concerned filled into bottles. Pharmaceutical organic or inorganic solid or liquid carriers suitable for oral, enteral or topical administration can be used to make up the composition. Gelatine, lactose, starch, magnesium stearate, talc, vegetable and animal fats and oils, gum polyalkylene glycol, or other known carriers for medicaments are all suitable as carriers. Furthermore, the compositions may contain other pharmaceutical active components which can appropriately be administered together with the compounds of the invention in the treatment of infectious diseases, such as other suitable antibiotics.

The invention will be further described in the following Examples:

EXAMPLE 1a

Pivaoyloxymethyl
6-[(hexahydro-1H-azepin-1-yl)-methyleneamino]-penicillanate 12.7 g of N-formylhexamethyleneimine was dissolved in 250 ml. of dry ether. While stirring and cooling, 8.5 ml. of oxalyl chloride in 50 ml. of dry ether was added dropwise. The mixture was stirred overnight at room temperature. The precipitated amide chloride was filtered off and washed with dry ether, and was placed in an exsiccator.

27.5 g of pivaloyloxymethyl 6-aminopenicillanate tosylate was suspended in 1500 ml. of ethyl acetate under continuous stirring and cooling in an ice bath. 950 ml. of ice-cold aqueous sodium bicarbonate (2 percent) was added. The ethyl acetate layer was separated and was shaken with 750 ml. of ice-water containing 25 ml. of aqueous sodium bicarbonate (2 percent), whereafter it was dried over magnesium sulfate at 0° C. After filtration the solution was evaporated to dryness in vacuo. The residue was dissolved in a solution 15.5 ml. of dry triethylamine in 75 ml. of dry alcohol-free chloroform. To this solution 10 g. of the above prepared amide chloride dissolved in 75 ml. of dry alcohol-free chloroform was added dropwise at a temperature of about $-20°$ C. After standing for half an hour at $-20°$ C., the temperature was raised to 0° C. within 15 minutes. The solution was evaporated to dryness in vacuo. The residue was stirred with 750 ml. of ether. Undissolved triethylamine hydrochloride was filtered off, and the filtrate was again evaporated to dryness in vacuo. The residue was reprecipitated from acetone (200 ml.)—water (150 ml.). After recrystallization from cyclohexane an analytically pure product was obtained with a melting point of 118.5°–119.5° C. and $[\alpha]_D^{20}$: +231° (c=1, 96% ethanol).

The starting material N-formylhexamethyleneimine was prepared from hexamethyleneimine and chloral and had a boiling point of 111°–112°/10 mm Hg.

EXAMPLE 2a

Pivaloyloxymethyl
6-(N,N-dimethylformamidino-N')-penicillanate hydrochloride 5.8 g of chlorodimethylformiminium chloride was dissolved in 40 ml. of dry alcohol-free chloroform. At a temperature of $-30°$ to $-40°$ C. this solution was added dropwise to a solution of 13.3 g. of pivaloyloxymethyl 6-aminopenicillanate and 12.4 ml. of triethylamine in 75 ml. of dry, alcohol-free chloroform while stirring. The temperature was raised to 0° C. within 1 hour. The solution was evaporated in vacuo and the residue was treated with 200 ml. of dry ether. After filtration from triethylamine hydrochloride, the filtrate was evaporated in vacuo. The oily residue was dissolved in 40 ml. of isopropanol. At 0° C. and while stirring, 4 ml. of a solution of dry hydrogen chloride in isopropanol (9N) was added dropwise. Thereafter 150 ml. of ether was added. After filtration, washing with ether and recrystallization from acetone-ether, the compound was obtained in analytically pure form having a melting point of 146° C. $[\alpha]_D^{20}$: +209° (c=1, 96% C$_2$H$_5$OH).

EXAMPLE 3a

Pivaloyloxymethyl
6-(N,N-dimethyl-phenylacetamidino-N')penicillanate nitrate 14 ml. of a solution of phosgene in dry toluene, containing 2.2 g of phosgene, was slowly to a solution of 3.3 g of N,N-dimethyl-phenylacetamide in 10 ml. of dry toluene with stirring and ice-cooling. Stirring was continued for 2 hours at room temperature, whereupon the amide chloride formed was quickly isolated by filtration with suction, washed with dry ether and kept in an exsiccator.

2.2 g of the crude amide chloride was dissolved in 35 ml. of dry, alcohol-free chloroform. While stirring and maintaining the temperature at $-30°$ C., this solution was slowly added to a solution of triethylamine (3.1 ml.) and pivaloyloxymethyl 6-aminopenicillanate in 15 ml. of dry, alcohol-free chloroform, prepared from 5.5 g of the p-toluenesulfonate of the amine as described in Example 1a. The temperature was raised to 0° C. during ¾ hour. After evaporating in vacuo, the residue was triturated with 200 ml. of ether. The precipitate was removed by filtration and the filtrate evaporated in vacuo. The residue was dissolved in 250 ml. of ether and filtered with "Dicalite" filter aid (diatomaceous earth).

0.35 ml. of concentrated nitric acid was dissolved in 10 ml. of dry ethanol and slowly added to the filtrate with stirring and ice-cooling. The precipitate formed was isolated and treated with 30 ml. of methylene chloride which leaves most of the nitrate of the unreacted pivaloyloxymethyl 6-aminopenicillanate undissolved. After filtration and evaporation in vacuo of the filtrate, the residue was twice recrystallized from acetone-ether yielding an analytically pure product with a melting point of 146.5°–147° C.. $[\alpha]_D^{20}$: 187° (c=1, 96% C$_2$H$_5$OH).

EXAMPLE 4a

Cyanomethyl
6-(N,N-diethylformamidino-N')-penicillanate oxalate

A. Cyanomethyl 6-aminopenicillanate p-toluenesulfonate

To a stirred suspension of 6-aminopenicillanic acid (43.3 g.) in dimethylformamide (400 ml.) at room temperature was added triethylamine (35 ml.) and chloroacetonitrile (25.5 ml.). Stirring was continued at room temperature for 24 hours. The mixture was diluted with 400 ml. of ethyl acetate, and filtered. The solid was washed with ethyl acetate. The filtrate was diluted with 800 ml. of ethyl acetate, extracted four times with 200 ml. of water and dried over magnesium sulfate. After filtration an 0.5M solution of p-toluenesulfonic acid in ethyl acetate (320 ml.) was added with stirring. The precipitate was filtered off and washed with ethyl acetate and ether. Recrystallization from methanol-ethyl acetate afforded a colourless analytically pure product, melting at 154.5°–156° C. (dec.) $[\alpha]_D^{20}$: +146° (c=1, 96% C$_2$H$_5$OH).

B. Chlorodiethylformiminium chloride 1.7 ml. of oxalyl chloride dissolved in 10 ml. of dry ether was slowly added to a solution of 2.2 ml. of diethylformamide in 50 ml. of dry ether at 0° C. with stirring. After stirring at room temperature for ¾ hour, the precipitate was quickly filtered with suction, washed with dry ether and stored in an exsiccator.

C. Cyanomethyl 6-(N,N-diethylformamidino-N')-penicillanate oxalate

Cyanomethyl 6-aminopenicillanate was liberated from 4.7 g. of the p-toluenesulfonate according to the procedure of Example 1 and dissolved in 15 ml. of dry, alcohol-free chloroform. Dry triethylamine (3.1 ml.) was added and the solution was cooled to −30° C. A solution of 1.7 g. of crude amide chloride in 15 ml. of dry, alcohol-free chloroform was slowly added at −20° C. to −30° C., with stirring. In the course of ¾ hour the temperature was allowed to raise to 0° C. The solution was evaporated in vacuo and the residue triturated with 200 ml. of ether. After filtration and evaporation in vacuo of the filtrate, the residue was dissolved in 200 ml. of ether and treated with "Dicalite" filter aid (diatomaceous earth). A solution of 0.85 g. of anhydrous oxalic acid in 50 ml. of ether was slowly added to the filtrate with stirring. When the precipitate had settled, the supernatant liquor was decanted and the precipitate stirred with fresh ether. After filtration, the product was recrystallized twice from acetone-ether to yield the analytically pure material melting at 121°-122.5° C. $[\alpha]_D^{20}$: +214° (c=1, 96% $C_2H_5OH$).

EXAMPLE 5a

γ-Phenylpropyl 6-[(hexahydro-1H-azepin-1-yl)-methyleneamino]-penicillanate hydrochloride

A. γ-Phenylpropyl 6-aminopenicillanate

To a stirred suspension of 6-aminopenicillanic acid (21.6 g.) in dimethylformamide (200 ml.) triethylamine (11.4 ml.) and γ-bromophenylpropane (22.0 g.) was added at room temperature. Stirring was continued at room temperature for 18 hours. 200 ml. of ethyl acetate was added and the mixture filtered. The filtrate was diluted with 400 ml. of ethyl acetate, extracted four times with 100 ml. of water and dried over magnesium sulfate. After evaporation in vacuo, the oily residue was dissolved in a mixture of water and ether (200 ml. of each) with stirring and ice-cooling. By slow addition of diluted hydrochloric acid the pH was adjusted to 3 to 4. The aqueous phase was separated, made alkaline to pH of about 7.5 by addition of sodium bicarbonate and extracted with ether. After drying, the ether was evaporated in vacuo to leave the crude ester as an oil.

B. γ-Phenylpropyl 6-[(hexahydro-1H-azepin-1-yl)-methyleneamino]-penicillanate hydrochloride 2.2 g. of the crude ester and 2.0 ml. of dry triethylamine were dissolved in 15 ml. of dry, alcohol-free chloroform and cooled to −60° C. with stirring. A solution of 1.2 g. of the amide chloride described in Example 1a in 10 ml. of dry, alcohol-free chloroform was slowly added. The temperature was raised to 0° C. during 1 hour, whereupon the solution was evaporated in vacuo. After trituration with 80 ml. of ether, the solid formed was filtered off. The filtrate was extracted with 80 ml. of water with stirring and ice-cooling, while the pH of the aqueous phase was lowered to about 3. The aqueous phase was separated, made alkaline with sodium bicarbonate and extracted with ether. After drying, the ether was evaporated in vacuo. The oily residue was dissolved in 10 ml. of isopropanol and treated with 0.35 ml of a solution of dry hydrogen chloride in isopropanol (9N), with stirring and ice-cooling. The precipitate was filtered off and washed with a little isopropanol. Two recrystallizations from methanol-ether yielded an analytically pure product melting at 163.5° C.. $[\alpha]_D^{20}$: +201 (c=1, 96% $C_2H_5OH$).

EXAMPLE 6a

6-[(Hexahydro-1H-azepin-1-yl)-methyleneamino]-penicillanic acid

A solution of the amide chloride described in Example 1a (4.6 g.) in dry, alcohol-free chloroform (20 ml.) was added slowly to a solution of trimethylsilyl 6-aminopenicillanate (7.2 g.) and triethylamine (3.5 ml.) in dry, alcohol-free chloroform (50 ml.) with stirring and cooling to −70° C. The temperature was raised to 0° C. during 1½ hours. The solution was evaporated to dryness in vacuo and the residue was triturated with dry ether (200 ml.). The precipitate was filtered off and washed with dry ether. The filtrate was diluted with ether (200 ml.). 2-Butanol (2.8 ml.) was added dropwise with stirring and cooling to 0° C. The stirring was continued for ¼ hour at 0° C., whereupon the precipitate was filtered off, washed with ether and dried. It was a white, amorphous powder, soluble in water. Paper chromatography was performed using the descending technique on Whatman No. 1 paper with the solvent system n-butaol-ethanol-water (4:1:5). The R$_f$ value was 0,5.

NMR spectrum (D$_2$O): $C_{(2)}(CH_3)_2$: 3H, s at 1.55. 3H, s at 1.68. $(CH_2)_4$: 8H, m at 1.4–2.0. $N(CH_2)_2$: 4H, m at 3.45–3.90. $C_{(3)}H$: 1H, s at 4.32. $C_{(5)}H$: 1H, d at 5.62, (J=4.0). $C_{(6)}H$: 1H, d at 5.47, (J=4.0). N—CH=N: 1H, broad s at 8.05.

The chemical shifts are given as ppm in δ values with sodium 2.2.3.3-tetradeutero-3-trimethylsilylpropionate (0 ppm) as internal standard. Coupling constants (J) are in cps.

EXAMPLES 7a to 31a

Following the procedure of the foregoing Examples, the compounds of Table I according to formula Va were obtained.

TABLE I $$\begin{array}{c} R_{1a} \quad R_{3a} \quad\quad S \quad CH_3 \\ \diagdown \quad | \quad\quad\quad / \diagdown / \\ N-C=N-CH-CH \quad C \\ / \quad\quad\quad | \quad\quad | \quad \diagdown \\ R_{2a} \quad\quad\quad\quad\quad\quad\quad\quad\quad CH_3 \\ \quad\quad\quad\quad O=C-N-\!\!\!-CH-COOCH_2OCOC(CH_3)_3, HX_a \end{array}$$

| Ex. No. | R$_{1a}$ | R$_{2a}$ | R$_{3a}$ | HX$_a$ |
|---|---|---|---|---|
| 7a | ethyl | ethyl | H | HNO$_3$ |
| 8a | propyl | propyl | H | HNO$_3$ |
| 9a | isopropyl | isopropyl | H | HNO$_3$ |
| 10a | allyl | allyl | H | HCl |
| 11a | methyl | n-butyl | H | HNO$_3$ |
| 12a | methyl | cyclopentyl | H | |
| 13a | methyl | cyclohexyl | H | |
| 14a | methyl | cycloheptyl | H | |
| 15a | methyl | benzyl | H | |
| 16a | methyl | p-chlorobenzyl | H | HNO$_3$ |
| 17a | pyrrolidyl-1 | | H | HNO$_3$ |
| 18a | piperidyl-1 | | H | |
| 19a | 2-methyl-piperidyl-1 | | H | HNO$_3$ |
| 20a | 3-methyl-piperidyl-1 | | H | |
| 21a | 4-methyl-piperidyl-1 | | H | |
| 22a | 2,6-dimethyl-piperidyl-1 | | H | |
| 23a | 1,2,3,4-tetrahydro-iso-quinolyl-2 | | H | |
| 24a | 4-methyl-piperazyl-1 | | H | (HNO$_3$)$_2$ |
| 25a | morpholinyl-4 | | H | HNO$_3$ |

TABLE I-continued $$R_{1a}\diagdown N-C(R_{3a})=N-CH-CH\diagup S\diagup C(CH_3)(CH_3)$$
$$R_{2a}\diagup \quad | \quad | $$
$$O=C-N-CH-COOCH_2OCOC(CH_3)_3, HX_a$$

| Ex. No. | $R_{1a}$ | $R_{2a}$ | $R_{3a}$ | $HX_a$ |
|---|---|---|---|---|
| 26a | hexahydro-1(2H)—azocinnyl | | H | |
| 27a | methyl | methyl | methyl | $HNO_3$ |
| 28a | methyl | methyl | n-propyl | $HNO_3$ |
| 29a | methyl | methyl | benzyl | $HNO_3$ |
| 30a | piperidyl-1 | | benzyl | $HNO_3$ |
| 31a | methyl | Pyrrolidylidene-2 | | $HNO_3$ |

In the Table II below are listed the physical constants of the compounds of Table I and the reaction conditions are shown:

TABLE II

Amide halide preparation.

| Ex. No. | Halogenating agent | Solvent | Reaction time in h. | Recrystallized from | M.p. °C. | Rotation $[\alpha]_D^{20}$ in ethanol (96%) |
|---|---|---|---|---|---|---|
| 7a | $(COCl)_2$ | Ether | 1 | Acetone-ether | 145–45.5 | +202 |
| 8a | $(COCl)_2$ | Ether | 2 | Acetone-ether | 121–22 | +196 |
| 9a | $(COCl)_2$ | Ether | 2 | Methanol-ether | 158.3–158.4 | +177 |
| 10a | $COCl_2$ | Toluene | 2 | Ethanol-ether | 131–131.5 | +205 |
| 11a | $(COCl)_2$ | Ether | 2 | Ethylacetate-ether | 124–125 | +188 |
| 12a | $(COCl)_2$ | Ether | 20 | Cyclohexane | 87–88 | +219 |
| 13a | $(COCl)_2$ | Ether | 5 | Ethanol-water | 73.5–74 | +202 |
| 14a | $(COCl)_2$ | Ether | 3–4 | Petrolether | 97–99 | +201 |
| 15a | $(COCl)_2$ | Ether | 2 | Acetone-water | 102–104 | +213 |
| 16a | $(COCl)_2$ | Ether | 16 | Methanol-ether | 163.5 | +183 |
| 17a | $(COCl)_2$ | Ether | 17.5 | Ethanol-ether | 116.5–17 | +182 |
| 18a | $(COCl)_2$ | Ether | 20 | Isoprop.-water | 102–03 | +206 |
| 19a | $(COCl)_2$ | Ether | 20 | Acetone-ether | 156.5–157 | +172 |
| 20a | $(COCl)_2$ | Ether | 20 | Petrolether | 70–71 | +209 |
| 21a | $(COCl)_2$ | Ether | 20 | Acetone-water | 96.5–97.5 | +218 |
| 22a | $(COCl)_2$ | Ether | 20 | Acetone-water | 91–93 | +205 |
| 23a | $(COCl)_2$ | Ether | 16.5 | Cyclohexane | 112–13 | +210 |
| 24a | $COCl_2$ | Toluene | 2 | Methanol-ether | 156.5–57 | +136 |
| 25a | $(COCl)_2$ | Ether | 19 | Methanol-ether | 148.5 | +167 |
| 26a | $(COCl)_2$ | Ether | 16 | Cyclohexane | 125.5 | +222 |
| 27a | $COCl_2$ | Toluene | 2.5 | Acetone-ether | 146.5–47 | +137 |
| 28a | $COCl_2$ | Toluene | 20 | Acetone-ether | 165–67 | +128 |
| 29a | $COCl_2$ | Toluene | 2 | Acetone-ether | 146.5–47 | +187 |
| 30a | $COCl_2$ | Toluene | 3 | Acetone-ether | 148–148.5 | +185 |
| 31a | $COCl_2$ | Toluene | 3 | Acetone-ether | 159–60 | +183 |

In a second method a compound of formula V is reacted with a compound of formula III—under conditions like those described for the reaction between II and III—to yield a new compound of the general formula VI:

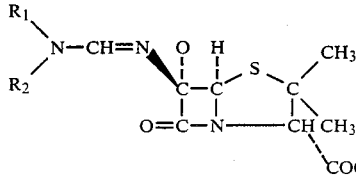

in which $R_1$ and $R_2$ are as defined above. These compounds are new and being interesting intermediates in the preparation of the compounds of this invention, they also constitute part of the invention.

Reaction between a compound of formula II and a compound of formula VI—under conditions like those described above for the reaction between IV and V—yields a compound of formula I.

In a third method a compound of formula VII:

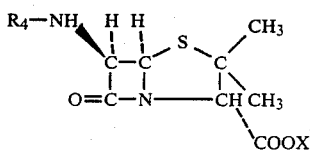

in which X is as defined above and $R_4$ represents a hydrogen atom or a protecting group such as trityl, carbobenzoxy or the like, is reacted with a compound of the above formula IV to yield a compound of the general formula VIII:

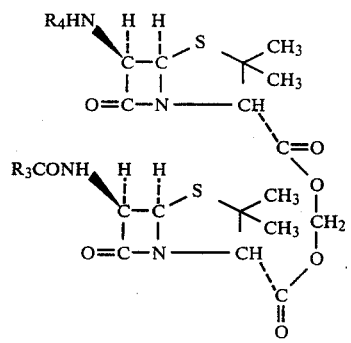

in which $R_3$ and $R_4$ are as defined above. The reaction conditions are similar to those described for the reaction between compounds of formula IV and V.

The compounds of formula VIII are described in the following section, or perhaps rather subsection, designated Section B. The compounds which it describes are in places described as "the compounds of the invention" or the like, but this is merely for convenience in designation and does not mean that they are among those compounds on which a patent is being sought in this application. To distinguish the formula numbers, the example numbers, the R numbers, and the like from those used elsewhere in this application, the suffix b has been appended to them in Section B. As will be noted, the compounds of formula VIIb are those of formula VIII when $R_{3b}$ is hydrogen and $R_4$ is hydrogen.

Section B as to the Compounds of formula VIII This invention relates to a series of penicillin esters, to salts thereof and to methods of their preparation.

The said penicillin esters have the general formula:

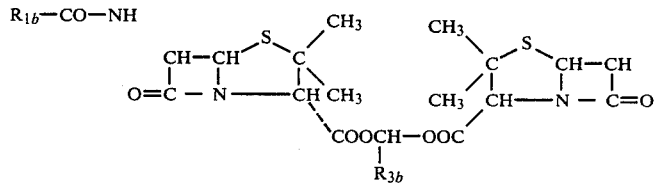

in which $R_{1b}$ and $R_{2b}$ are radicals known from biosynthetic, semi-synthetic and naturally occurring penicillins, such as alkyl, aryl or aralkyl radicals optionally substituted with hydroxy and etherified hydroxy, halogen, amino, azido, heterocyclic or spirocyclic radicals, for instance a benzyl radical, a phenoxymethyl radical, a dimethoxyphenyl radical, an alpha-azidobenzyl radical, an alpha-aminobenzyl radical, a beta-amino-alpha-phenylethyl radical, an alpha-amino-spirocyclopentyl radical, and other radicals containing one or two amino groups. $R_{1b}$ and $R_{2b}$ may represent the same or different radicals but at least one of them shall contain an amino group; $R_{3b}$ is hydrogen or a lower alkyl radical, a halo-lower alkyl radical, an aryl radical or an aralkyl radical, such as methyl, ethyl, propyl, isopropyl, trichloromethyl, trifluoromethyl, phenyl and benzyl radicals.

The salts of the said compounds are salts with inorganic or organic pharmaceutically acceptable acids such as hydrochloric acid, hydrobromic acid, sulfuric acid, phosphoric acid, tartaric acid, citric acid, fumaric acid, maleic acid and the like acids.

When $R_{1b}$ and/or $R_{2b}$ contain asymmetric carbon atoms or when $R_{3b}$ is different from hydrogen and $R_{1b}$ different from $R_{2b}$ the compounds of the invention will exist in different epimeric forms and the invention comprises these epimers as well as mixtures thereof. The form in which the compounds are obtained depends on which enantiomer of the starting materials and which method is used to make the compounds. The mixtures of the epimeric forms may be separated by fractional crystallization or other known methods.

In contrast to the corresponding free penicillins the compounds of the invention are efficiently absorbed from the gastro-intestinal tract and after the absorption they are rapidly transformed into the corresponding free penicillins, either spontaneously or under the influence of enzymes present in the body.

According to experiments carried out in connection with the present invention it has been demonstrated in animal tests that upon oral administration of penicillin esters of formula (Ib) extremely high concentrations of the corresponding free penicillin(s) are found in blood and tissues due to efficient absorption combined with rapid hydrolysis in the organism. Thus, the present penicillin esters are in particular proposed for oral administration in treatment of patients suffering from infectious diseases which require a high level of antibiotic activity in blood and tissues. In such cases, the desirable high concentration of the known penicillins is normally obtained by administration by the parenteral route which is inconvenient to the patient if the treatment is prolonged, and impractical for the medical practitioner.

The compounds of formula (Ib), are well tolerated compounds which are administered in clinical practice either as such or, preferably, in the form of one of their salts mixed with carriers and/or auxiliary agents and in any suitable form of pharmaceutical presentation for oral use.

In such compositions, the proportion of therapeutically active material to carrier substance and auxiliary agent can vary between 1% and 95%. The compositions can either be worked up to pharmaceutical forms of presentation such as tablets, pills or dragees, or can be filled in medical containers such as capsules, or as far as mixtures are concerned, filled into bottles. Pharmaceutical organic or inorganic, solid or liquid carriers suitable for oral, enteral or topical administration can be used to make up the composition. Gelatine, lactose, starch, magnesium stearate, talc, vegetable and animal fats and oils, gum, polyalkylene glycol, or other known carriers for medicaments are all suitable as carriers. The preferred salt of the esters in the hydrochloride but salts with other inorganic or organic acids may be used as mentioned above. Furthermore, the compositions may contain other pharmaceutically active components which can appropriately be administered together with the ester in the treatment of infectious diseases, such as other suitable antibiotics.

The compounds of the invention can be prepared by reacting a salt of a penicillin of the general formula IIb with a compound of the general formula IIIb

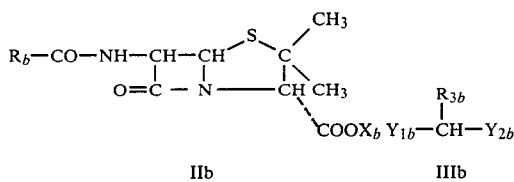

IIb   IIIb in which formulae $R_b$ represents either $R_{1b}$ or $R_{2b}$ which are as defined above, or a radical which can be converted into $R_{1b}$ or $R_{2b}$ such as radicals containing a protected amino group or a group which can be converted into an amino group e.g. azido, nitro or halogen; $X_b$ is a cation such as a potassium, sodium, ammonium or trialkylammonium ion, and $Y_{1b}$ and $Y_{2b}$ individually represent chlorine, bromine, iodine, alkylsulfonyloxy or arylsulfonyloxy groups. The compounds of formula IIIb are, for instance, methylene iodide, methylene bromide, chloroiodomethane, bis-methanesulfonyloxy methane or bis-toluenesulfonyloxymethane. In the case where the $Y_{1b}$ and $Y_{2b}$ are the same, the reaction with a compound of formula IIb gives compounds of formula IVb

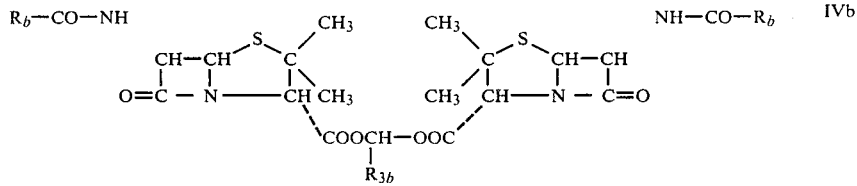

in which $R_b$ contains one or more protected amino groups or groups which can be converted into an amino group. From these intermediates the compounds of the invention in which $R_{1b}$ and $R_{2b}$ are the same are obtained after cleavage of the protecting group or by conversion of one of the groups mentioned above into an amino group. Compounds of the invention in which $R_{1b}$ and $R_{2b}$ are different may also be produced by reacting the corresponding penicillin salts, if necessary in a protected form, in two steps with a compound of formula IIIb($Y_{1b}\neq Y_{2b}$) when an excess of that compound is used and the reaction is performed under sufficiently careful and mild conditions. It is, however, more advantageous in these cases to use compounds of formula IIIb in which $Y_{1b}$ and $Y_{2b}$ are different, for example chloroiodomethane because the reactivity of the chlorine atom is less than that of the iodine atom, and the first reaction step therefore, yields an ester of the penicillin used in the reaction having the formula Vb:

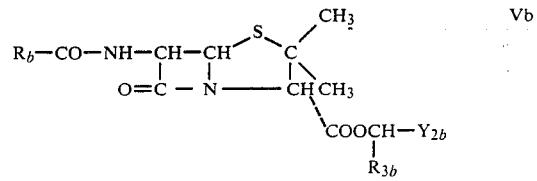

Compounds of formula Vb react easily with a penicillin salt of formula IIb in which $R_b$ may be the same as, or different from, the first $R_b$, whereby intermediates of formula IVb are obtained. These can be converted into the compounds of the invention as described above. The reactions are performed in inert organic solvents such as dimethylformamide or acetone and at room temperature or at slightly elevated temperatures. In some cases the intermediates of formula IVb are not isolated but directly converted into the compounds of the invention. The isolation of the reaction products is done in usual manner and if the epimers are to be separated this can be done, for instance, by means of fractional crystallization in suitable solvents.

It will appear from the description above that in the case where amino groups are present in the $R_{1b}$ and $R_{2b}$ radicals, these amino groups are preferably protected during the reactions or are replaced by groups which can be converted to amino groups as a last step of the synthesis.

As a common characteristic of such groups, which in the following are called $Z_b$ it can be said that $Z_b$ is selected from groups which are capable of being converted to an amino group by means of methods mild enough to avoid destruction of the molecule at the ester group or at the lactam ring. In particular, $Z_b$ is a benzyloxycarbonyl-amino radical, a p-halo-, p-nitro-, or p-methoxy-benzyloxy-carbonyl-amino radical, a $\beta,\beta,\beta$-trichloro-ethoxycarbonyl-amino or an allyloxycarbonyl-amino radical; or $Z_b$ is a sulphur containing radical, such as tritylsulphenyl-amino or arylsulphenylamino radical, i.e. an o-nitrophenylsulphenyl-amino radical; $Z_b$ may also be a tritylamino radical, a tertiary butoxycarbonyl-amino radical, or a radical obtained by reacting the free amino group with a $\beta$-dicarbonyl compound such as acetylacetone, an acetoacetic ester or benzoylacetone to form enamines or Schiff bases. In general, any group represented by $Z_b$ which can be converted by reduction, by mild acid hydrolysis or by other mild reactions known per se, into an amino group will be suitable, since experiments have shown that the esters of formula Ib formed by the reaction in question are stable under such conditions.

The conversion of $Z_b$ into an amino group can be effected by different procedures depending on what $Z_b$ stands for. Catalytic hydrogenation will be preferred when $Z_b$ stands for benzyl-oxycarbonyl-amino and related derivatives thereof, and for trityl-amino. This hydrogenation is preferably performed at room temperature and at atmospheric or slightly elevated pressure in a solvent which may be a non-reducible organic solvent or a mixture thereof with water. The preferred catalysts are noble metal catalysts such as palladium or platinum or Raney-Nickel, but other catalysts can also be used. Electrolytic reduction can also be used in these cases. When $Z_b$ stands for a $\beta,\beta,\beta$-trichloroethoxycarbonylamino radical, reduction with zinc in acetic acid is preferred. A mild acid hydrolysis is preferred in the case where $Z_b$ stands for a sulphur-containing radical, an enamine or a Schiff base, for instance at a pH of about 2 in a diluted solution of hydrogen chloride preferably in aqueous tetrahydrofurane. An acid hydrolysis, for instance with hydrochloric acid, acetic acid, p-toluenesulfonic acid or trifluoroacetic acid can also be used for elimination of the trityl and tert.butoxycarbonyl radical. Also known from the literature is the removal of the o-nitrophenylsulphenyl radical involving a nucleophilic attack on the sulphur atom of the sulphenamide group, the best yield in the present case being obtained with sodium or potassium iodide, sodium thiosulphate, sodium hydrogen sulphite, sodium dithionite or potassium thiocyanate. Other sulphenamide radicals can be split in the same way. If $Z_b$ is an azido or a nitro group or a halogen atom, especially a bromine atom, these groups may be transformed into the free amino group in a known manner, the azido and the nitro group by a catalytic hydrogenation with a noble metal catalyst or with Raney-Nickel or by an electrolytic reduction, and the halogen atom by an amination, for instance with hexamethylenetetramine.

In the case where one or both of the radicals $R_{1b}$ and $R_{2b}$ contain a free hydroxy group it can be protected during the reaction by generally known methods, e.g. by etherification or acylation.

The compounds of the invention can also be prepared from 6-aminopenicillanic acid which, in the form of a salt, reacts with the compounds of formula IIIb to form an ester of the following formula VIb:

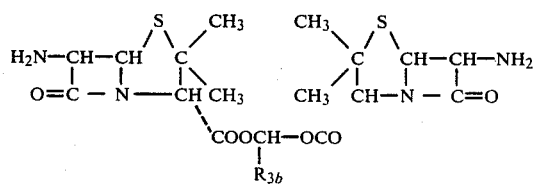

in which $R_{3b}$ is as defined above.

The amino groups are preferably, but not necessarily, protected for instance with a triphenylmethyl radical and the process can be performed under reaction conditions similar to those described above for the reaction between compounds of formulae IIb and IIIb.

The above compounds of formula VIb can also be produced by reacting salts of industrially available penicillins, for example benzylpenicillin, with a compound of formula IIIb under the reaction conditions already described to yield a compound of formula IVb in which $R_b$ is e.g. benzyl. The side chains of these compounds are subsequently split off enzymatically or chemically. The preferred method consists of reacting the 6-acylamino-penicillanic acid ester with an acid halide in the presence of an acid-binding agent, such as quinoline or pyridine, and the like. The preferred acid halide is, however, phosphorus pentachloride, because the reaction in this case can be performed at low temperature increasing the stability of the intermediate formed, which presumably is an imino halide. The reaction can be performed in different solvents, but the preferred are chloroform and methylene chloride.

The intermediate is not isolated but is treated with an excess of a primary alcohol to form an imino ether. The reaction temperature and the reaction time depend on the alcohol used; in most cases temperatures from $-20°$ C. to $+20°$ C. will be convenient.

The imino ether is not isolated, but subjected to an acid alcoholysis or hydrolysis, whereby the C=N bond is cleaved to yield the corresponding 6-amino-penicillanic ester of formula VIb. It is surprising that the lactam ring and the acyloxymethyl ester grouping are sufficiently stable under these conditions. By the generally used methods the esters of 6-amino-penicillanic acid can be isolated from the reaction mixture as such or in the form of a salt with an inorganic or organic acid such as the hydrochloride or the tosylate.

The compounds of formula VIb are such and being important intermediates in the preparation of the compounds of the invention they also constitute a part of this invention.

In the method of preparing the intermediates of formula VIb, $Y_{1b}$ and $Y_{2b}$ in the compounds of formula IIIb can be the same or different. If $Y_{1b}$ is substantially more reactive than $Y_{2b}$ the reaction will be a two-step process and the first reaction product will be an $\alpha$-$Y_{2b}$ ester of 6-amino-penicillanic acid or a protected 6-amino-penicillanic acid. Both these esters and the above described corresponding esters of formula Vb are such compounds which also constitute a part of this invention. It is evident that they are especially valuable intermediates for the preparation of compounds of the invention in which $R_{1b}$ and $R_{2b}$ are different. The esters of 6-aminopenicillanic acid in free or protected form can be reacted with a salt of a penicillin of formula IIb whereby, if necessary after elimination of of a protecting group on the amino group, a compound of the following formula VIIb is obtained:

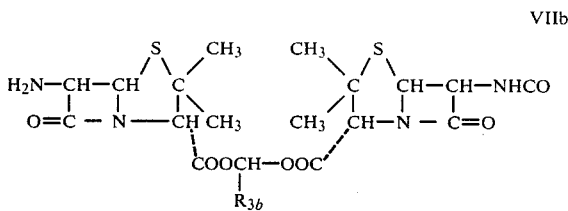

in which $R_b$ and $R_{3b}$ are as defined above. Compounds of formula VIIb can also be obtained from compounds of formula IVb in which $R_b$ e.g. is benzyl by a modification of the method used for removal of the side chain described above.

These intermediates can thereafter be reacted with reactive derivatives of acids of the formula $R_b$-COOH such as acid halides, acid anhydrides or mixed anhydrides in which $R_b$ is as defined above, whereby the compounds obtained are either the compounds of the invention or the corresponding compounds having protected groups which, in the manner already described, can be converted to the compounds of the invention.

The invention will now be illustrated by the following Examples:

EXAMPLE 1b

A.
Bis-[6β-(D-α-azidophenylacetamido)-penicillanoyloxy]-methane

A mixture of potassium D-α-azidobenzylpenicillinate (10.0 g.) and chloroiodomethane (1.0 ml.) in dimethylformamide (DMF) (50 ml.) is stirred for 3 days at room temperature.

Thereafter, the mixture is diluted with ethyl acetate, filtered, and the filtrate washed with water, aqueous sodium bicarbonate and water. The organic phase is dried and evaporated in vacuo to yield the desired product as a brownish amorphous product, which could be used for the next step without further purification.

The IR-spectrum (CHCl$_3$) shows strong band at: 2110, 1780, 1690 and 1510 cm$^{-1}$.

The NMR-spectrum (CDCl$_3$) shows signals at δ=1.53 and 1.65 (2s), 4.50 (s), 5.13 (s), 5.50–5.90 (m), 5.90 (s), 7.15 (d), J=10, 7.42 (s) (TMS as internal standard).

B.
Bis-[6β-(D-α-aminophenylacetamido)-penicillanoyloxy]-methane, dihydrochloride A solution of bis-[6β-(D-α-azidophenylacetamido)-penicillanoyloxy]-methane (5.1 g.) in ethyl acetate (100 ml.) is placed in a three-necked 500 ml. flask equipped with a gas inlet-outlet tube, a glass-calomel combination electrode, a burette and a magnetic stirrer. Water (100 ml.) and 10% palladium on carbon catalyst (3 g.) are added. The system is flushed with nitrogen, whereafter a stream of hydrogen is bubbled through the suspension while stirring, a pH-value of 2.5 being maintained in the suspension by the addition of 0.5N hydrochloric acid (40 ml.). When the consumption of acid has ceased, the catalyst is filtered off. The aqueous phase is separated and freeze-dried to afford the desired compound as a colourless amorphous product.

The IR-spectrum (KBr) shows strong bands at: 1770–1790 (broad) and 1690 cm$^{-1}$.

The NMR-spectrum (CD$_3$OD) shows signals at δ=1.42 and 1.47 (2s), 4.43 (s), 5.18 (s), 5.55 (dd, J=4.5), 5.90 (s), 7.53 (s). (TMS as internal standard).

EXAMPLE 2b

A.
6β-(D-α-azido-α-phenylacetamido)-penicillanoyloxymethyl phenoxymethylpenicillinate To a solution of chloromethyl phenoxymethylpenicillinate (0.4 g.)—prepared as described below—in dimethylformamide (6 ml.) is added potassium D-α-azidobenzylpenicillinate (0.42 g.). After stirring overnight at room temperature, the mixture is diluted with ethyl acetate (20 ml.) and extracted with water (2×5 ml.), 2% aqueous sodium bicarbonate (5 ml.) and water (2×5 ml.). The organic phase is dried and evaporated to dryness in vacuo to yield the desired compound as an amorphous powder.

The IR-spectrum (CHCl$_3$) shows strong bands at 2130, 1785, 1693, 1515, 1498 and 980 cm$^{-1}$.

The NMR-spectrum (CDCl$_3$) shows peaks at δ=1.53 (s), 1.60 (s), 1.66 (s), 4.50 (s), 4.55 (s), 5.13 (s), 5.40–5.90 (m), 5.90 (s), 6.80–7.50 (m) and 7.43 (s), TMS being used as internal reference.

Preparation of the starting material

Chloromethyl phenoxymethylpenicillinate

To a solution of phenoxymethylpenicillin (70 g.) and triethylamine (29.4 ml.) in dimethylformamide (250 ml.) is added chloroiodomethane (80 ml.), and the mixture is stirred for 3.5 hours at room temperature. Thereafter, the mixture is diluted with ethyl acetate (500 ml.) and ether (500 ml.), filtered, and the filtrate washed with water (3×250 ml.), 0.5M aqueous sodium bicarbonate (100 ml.), and water (2×100 ml.). The organic phase is dried and evaporated in vacuo to yield the crude ester as a brownish gum, which can be used for the next step without further purification.

B.
6β-(D-α-amino-α-phenylacetamido)-penicillanoyloxymethyl phenoxymethylpenicillinate hydrochloride This compound is obtained from 6β-(D-α-azido-α-phenylacetamido)-penicillanoyloxymethyl phenoxymethylpenicillinate by catalytic reduction, performed as described in Example 1b B. The aqueous phase is separated and freeze-dried to afford the desired compound as a colourless amorphous powder.

The IR-spectrum (KBr) shows strong bands at 1780, 1690, 1515, 1495, 1292, 1240, 1205, and 977 cm$^{-1}$.

The NMR-spectrum (CD$_3$OD) shows peaks at δ=1.45 (s), 1.48 (s) 1.53 (s), 1.60 (s), 4.47 (s), 4.57 (s), 4.65 (s), 5.17 (s), 5.40–5.80 (m), 5.95 (s), 6.90–7.80 (m) and 7.55 (s), TMS being used as internal reference.

EXAMPLE 3b

A.
6β-(D-α-azido-α-phenylacetamido)-penicillanoyloxymethyl benzylpenicillinate To a solution of chloromethyl benzylpenicillinate (2 g.)—prepared as described below—in dimethylformamide (30 ml.) is added potassium D-α-azidobenzylpenicillinate (2.1 g.).

After stirring overnight at room temperature the mixture is diluted with ethyl acetate (100 ml.) and extracted with water (2×25 ml.), 2% aqueous sodium bicarbonate (25 ml.) and water (2×25 ml.). The organic phase is dried and evaporated to dryness in vacuo to yield the desired compound as an amorphous powder.

The IR-spectrum (CHCl$_3$) shows strong bands at 2130, 1785, 1688, 1510, 1295 and 980 cm$^{-1}$.

The NMR-spectrum (CDCl$_3$) shows peaks at δ=1.47 (s), 1.52 (s), 1.63 (s), 3.63 (s), 4.42 (s), 4.48 (s), 5.13 (s), 5.40–5.90 (m), 5.88 (s), 7.33 (s), and 7.43 (s). (TMS being used as internal standard).

Preparation of the starting material

Chloromethyl benzylpenicillinate

To a suspension of triethylammonium benzylpenicillinate (44 g.) in dimethylformamide (400 ml.) is added chloroiodomethane (40 ml.).

After stirring overnight the mixture is diluted with ethyl acetate (1200 ml.) and extracted with water (2×400 ml.) 2% aqueous sodium bicarbonate (100 ml.) and finally water (2×200 ml.).

The organic phase is dried, filtered and the filtrate evaporated in vacuo to give chloromethyl benzylpenicillinate as a dark, viscous oil.

The crude material is purified by dry column chromatography on silica gel (cyclohexane:ethyl acetate 7:3)

and the pure chloromethyl benzylpenicillinate thus obtained is crystallized from ether:petroleum ether to yield colourless crystals with m.p. 92°–93° C.

$[\alpha]_D^{20} = +179.8°$ (c=1, CHCl$_3$).

The IR spectrum (KBr) shows strong bands at: 1785, 1770, 1655, 1547, 1303, 1139, 1118 and 712 cm$^{-1}$.

The NMR-spectrum (CDCl$_3$) shows signals at δ=1.51 (s), 3.64 (s), 4.41 (s), 5.53 (d, J=5), 5.68 (dd, J=5, J=9), 5.69 (d, J=6), 5.85 (d, J=6), 6.2 (d, J=8–9), and 7.35 (s) ppm. TMS is used as internal reference.

B.

6β-(D-α-amino-α-phenylacetamido)-penicillanoyloxymethyl benzylpenicillinate, hydrochloride This compound is obtained from 6β-(D-α-azido-α-phenylacetamido)-penicillanoyloxymethyl benzylpenicillinate by catalytic reduction, performed as described in Example 1b B. The aqueous phase is separated and freeze-dried to afford the desired compound as a colourless amorphous powder.

The IR-spectrum (KBr) shows strong bands at 1775, 1685, 1510, 1498, 1295, 1245, 1195, 1170, 1140 and 980 cm$^{-1}$.

The NMR-spectrum (CD$_3$OD) shows peaks at δ=1.43 (s), 1.47 (s) 1.48 (s), 1.62 (s), 3.62 (s), 4.44 (s), 4.50 (s), 5.17 (s), 5.40–5.80 (m), 5.92 (s), 7.32 (s) and 7.52 (s). (TMS being used as internal standard).

Analogously to the procedure described in Example 3b A the following compounds are prepared from potassium D-α-azidobenzylpenicillinate and the chloromethyl esters of 2,6-dimethoxyphenylpenicillin, 5-methyl-3-phenyl-4-isoxazolylpenicillin, 3-(-o-chlorophenyl)-5-methyl-4-isoxazolylpenicillin, and 3-(2,6-dichlorophenyl)-5-methyl-4-isoxazolylpenicillin:

6β-(D-α-azido-α-phenylacetamido)-penicillanoyloxymethyl 2,6-dimethoxyphenylpenicillinate 6β-(D-α-azido-α-phenylacetamido)-penicillanoyloxymethyl 5-methyl-3-phenyl-4-isoxazolylpenicillinate 6β-(D-α-azido-α-phenylacetamido)-penicillanoyloxymethyl 3-(o-chlorophenyl)-5-methyl-4-isoxazolylpenicillinate 6β-(D-α-azido-α-phenylacetamido)-penicillanoyloxymethyl 3-(2,6-dichlorophenyl)-5-methyl-4-isoxazolylpenicillinate These compounds are converted into the hydrochlorides of the corresponding amino-compounds by reduction of the azido groups as described in Example 1b B.

EXAMPLE 4b

A.

Bis-(6β-phenylacetamido-penicillanoyloxy)-methane

To a stirred suspension of potassium benzylpenicillinate (22.3 g.) in dimethylformamide (110 ml.) is added chloroiodomethane (5.3 g.). After stirring for 48 hours at room temperature the mixture is diluted with ethyl acetate (330 ml.) and extracted with water (2×60 ml.), 2% aqueous sodium bicarbonate (60 ml.) and water (2×60 ml.).

The organic phase is dried and evaporated to dryness in vacuo to yield the desired compound as an amorphous powder.

The IR-spectrum (CHCl$_3$) shows strong bands at 1780, 1675, 1505, 1290, 1135 and 982 cm$^{-1}$.

The NMR-spectrum (CDCl$_3$) shows peaks at δ=1.45 (s), 3.63 (s), 4.39 (s), 5.60–5.80 (m), 5.85 (s), 6.20 (d) and 7.33 (s). (TMS being used as internal standard).

B. 6β-amino-penicillanoyloxymethyl benzylpenicillinate

To a solution of PCl$_5$ (0.97 g.) in dry, alcoholfree CHCl$_3$ (25 ml.) is added quinoline (1.07 ml.) with stirring. The solution is cooled to −10° C. and bis-(6β-phenylacetamido-penicillanoyloxy)-methane (1.36 g.) is added. After stirring for 15 minutes at −10° C. n-propyl alcohol (5.1 ml.) is added. The temperature is kept at −10° C. for a further 15 minutes. Then the mixture is poured into water (25 ml.) and petroleum ether (55 ml.) is added.

The aqueous phase is separated and the pH adjusted to 7.5 by addition of sodium bicarbonate. The aqueous phase is extracted with ether (25 ml.). The organic phase is separated dried and evaporated to dryness in vacuo to yield a mixture of the desired compound and quinoline.

Extraction of the residue with petroleum ether (3×10 ml.) removes the quinoline and leaves the desired compound as an amorphous powder.

The NMR-spectrum (CDCl$_3$) shows peaks at δ=1.45 (s), 1.50 (s), 1.63 (s), 2.25 (broad singlet), 3.63 (s), 4.42 (s), 4.58 (d), J=4.5, 5.40–5.80 (m), 5.87 (s), and 7.33 (s). (TMS being used as internal standard).

C.

6β-(D-α-azido-α-phenylacetamido)-penicillanoyloxymethyl benzylpenicillinate

A solution of 6β-amino-penicillanoyloxymethyl benzylpenicillinate (2.81 g.) and triethylamine (0.73 ml.) in ethyl acetate (30 ml.) is cooled to +5° C. During 15 minutes a solution of D-α-azidophenylacetyl chloride (1.01 g.) in ethyl acetate (10 ml.) is added with stirring. The mixture is stirred for a further 30 minutes at +5° C. and then at room temperature for 1 hour. The mixture is washed with water, 0.01N hydrochloric acid, 2% aqueous sodium bicarbonate and finally water. The organic phase is dried and evaporated in vacuo to yield the desired compound as an amorphous powder, identical with the compound described in Example 3b A.

EXAMPLE 5b

A. Bis-(6β-amino-penicillanoyloxy)-methane

To a solution of PCl$_5$ (1.28 g.) in dry, alcohol-free CHCl$_3$ (30 ml.) is added quinoline (1.46 ml.) with stirring. The solution is cooled to −10° C. and bis-(6β-phenylacetamido-penicillanoyloxy)-methane (1.36 g.) is added. After stirring for 15 minutes at −10° C. n-propyl alcohol (6.6 ml.) is added. The temperature is kept at −10° C. for a further 15 minutes. Then the mixture is poured into water (50 ml.) and petroleum ether (110 ml.) is added.

The aqueous phase is separated and the pH adjusted to 7.5 by addition of sodium bicarbonate. The aqueous phase is then extracted with ethyl acetate (3×25 ml.).

The organic phases are collected, dried and evaporated to dryness in vacuo to yield a mixture of the desired compound and quinoline. Extraction of the residue with petroleum ether (3×15 ml.) removes the quinoline and leaves the desired compound as an amorphous powder.

The NMR-spectrum (CDCl$_3$) shows peaks at δ=1.53 (s), 1.65 (s), 1.90 (broad singlet), 4.43 (s), 4.60 (d), J=4.5, 5.50 (d), J=4.5 and 5.90 (s). (TMS being used as internal standard).

B.
Bis-[6β-(D-α-azido-α-phenylacetamido)-penicillanoyloxy]methane

A solution of bis-(6β-amino-penicillanoyloxy)-methane (1.15 g.) and triethylamine (0.73 ml.) in ethyl acetate (20 ml.) is cooled to +5° C. During 15 minutes a solution of D-α-azidophenylacetyl chloride (1.01 g.) in ethyl acetate (10 ml.) is added with stirring. The mixture is stirred for a further 30 minutes at +5° C. and then at room temperature for 1 hour. The mixture is washed with water, 0.01N hydrochloric acid, 2% aqueous sodium bicarbonate and water. The organic phase is dried and evaporated in vacuo to yield the desired compound as an amorphous powder, identical with the compound described in Example 1A.

In the case where $R_4$ represents a hydrogen atom the intermediates of formula VIII can be used directly in the next step, and if $R_4$ represents a protective group this is first removed, e.g. by hydrogenation or hydrolysis.

In a next step the compounds of formula VIII ($R_4$=H) are reacted with a reactive derivative of an amide or a thioamide of the general formula IX:

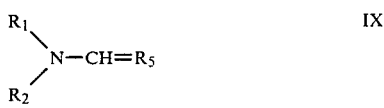

in which $R_1$ and $R_2$ have the meanings defined before, and $R_5$ stands for O or S to yield the compounds of formula I.

The starting materials of formula IX are known or can be prepared by methods known from generally used textbooks.

The amides of formula IX can by well-known methods be transferred into reactive derivatives such as acid amide halides, acid amide dialkyl sulphate complexes or acid amide acetals. The acid amide halides used are preferably the chlorides or bromides, and they can be prepared by treating the amides with halogenating agents. It is preferred to use halogenating agents which throughout the reaction form gaseous by-products, such as phosgene, oxalyl halides, or thionyl halides, but also others may be used. The reaction can be performed in inert, dry, organic solvents, e.g. ether or toluene, in which the amide halide in most cases will be insoluble and from which it can be isolated by filtration after the reaction is completed. The acid amide halides are hygroscopic and rather unstable and are therefore preferably used in the next step without purification.

The acid amide dialkyl sulphate complexes can be prepared by treating the amides with dialkyl sulphate, preferably dimethyl sulphate, under well-known conditions. By treating the acid amide dialkyl sulphate complexes with sodium lower alcoholates, e.g. sodium methoxide, acid amide acetals of the general formula IXa:

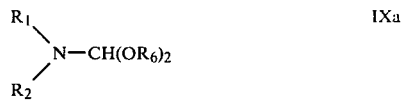

in which $R_1$ and $R_2$ have the meanings defined above and $R_6$ is a lower alkyl group, are formed, which acetals may also be used in the next step.

When acid thioamides are used as starting materials a reactive derivative in form of an acid thioamide alkyl halide complex can be formed by treatment with alkyl halides, e.g. lower-alkyl iodide. This reaction is well-known from the chemical literature.

The reaction conditions for the reaction between the amide derivative and the compound of formula VIII depend on the reaction components used in the process. When acid amide acetals are used in the reaction with the compounds of formula VIII, the reaction temperature depends on the reaction components. The reaction is performed in inert organic solvents, for instance ether.

When acid amide halides, dialkyl sulphate complexes, or thioamide alkyl halide complexes are used, the reaction is also performed in inert organic solvents, which are dry and free from traces of alcohols, preferably chloroform, in which the reaction components are soluble, but solvents in which the starting materials are insoluble, e.g. ether, may be used as well. The reaction is performed under cooling and in the presence of at least one equivalent of a tertiary amine, for example trimethylamine, triethylamine, N,N-diisopropylethylamine or N-methylmorpholine. In the case where one equivalent of the tert.amine is used, the reaction product will be obtained as a salt when an acid amide halide is used, and as the free esters of formula I when the dialkyl sulphate complexes and thioamide alkyl halide complexes are used.

The reaction time depends on the reactants, the temperature and the solvents used in the process.

In another embodiment of the method a compound of the above formula VI is reacted with a compound of the above formula VII under the same conditions as described above for the reaction between the compounds of formula IV and formula VII to yield a compound of formula X:

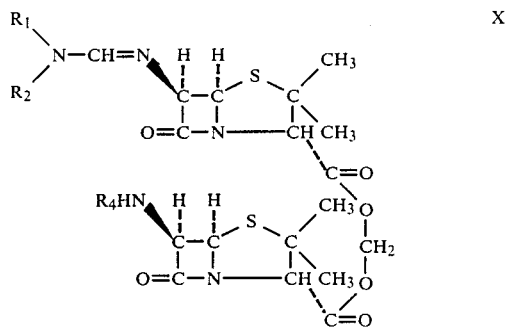

in which $R_1$, $R_2$ and $R_4$ have the above defined meanings. In the case when $R_4$ is different from hydrogen this protecting group has to be split off whereafter the reaction product of formula X, ($R_4$=H), is acylated with a reactive derivative of an acid $R_3$—COOH in which $R_3$ is as above defined to yield the compounds of the invention. This acylation process is well-known from the preparation of other semi-synthetic penicillins.

The invention will be further described in the following Examples which are not to be construed as limiting the invention.

EXAMPLE 1

6-[(Hexahydro-1H-azepin-1-yl)-methyleneamino]-penicillanoyloxymethyl benzylpenicillinate To a suspension of sodium 6-[(hexahydro-1H-azepin-1-yl)-methyleneamino]-penicillanate (3.5 g.) in dimethylformamide (50 ml.) was added chloromethyl benzylpenicillinate (3.8 g.). After stirring at room temperature for 65 hours the mixture was diluted with ethyl acetate (200 ml.) and washed with water (3×25 ml.). The organic phase was extracted with dilute hydrochloric acid (pH=2.5). The aqueous phase was separated and made alkaline by adding sodium bicarbonate. The oil which separated was taken up in ethyl acetate and the solution was dried and evaporated to dryness in vacuo to yield the desired compound as an amorphous powder.

The NMR-spectrum (CDCl$_3$) showed peaks at $\delta$=1.47 (s), 1.65 (s), 1.58 (m), 3.37 (m), 3.63 (s), 4.38 (s), 4.40 (s), 5.08 (dd), 5.4–5.8 (m), 5.87 (s), 6.20 (d), 7.32 (s) and 7.59 (d) ppm. TMS was used as internal reference. The IR-spectrum (CHCl$_3$) showed strong bands at 1773, 1673 and 1630 cm$^{-1}$.

The starting materials used in the above example are prepared in the following manner:

6-[(Hexahydro-1H-azepin-1-yl)-methyleneamino]-penicillanic acid dihydrate

A. 1-Hexamethyleneiminecarboxaldehyde dimethyl acetal was prepared from the N-formylhexamethyleneimine-dimethyl sulfate complex by reaction with sodium methoxide according to the method of Bredcreck et al. (Chem. Ber. 101, 41 (1968)). The boiling point was 83°–84° C./12 mm Hg.

B. 6-[(Hexahydro-1H-azepin-1-yl)-methyleneamino]-penicillanic acid dihydrate. A solution of the above mentioned acid amide acetal (4.1 g.) in dry ether (100 ml.) was slowly added to a solution of trimethylsilyl 6-aminopenicillanate (6.8 g.) in ether (500 ml.) at −30° C. with stirring. The temperature was raised to 0° C. within half an hour. Water (300 ml.) was added. The stirring was continued for ten minutes whereafter the aqueous phase was separated, extracted with ether and freezedried. The solid product was crystallized from methanol-acetone. It melted with decomposition from 135° to 142° C.

Sodium 6-[(hexahydro-1H-azepin-1-yl)-methyleneamino]-penicillanate

To a solution of 6-[(hexahydro-1H-azepin-1-yl)-methyleneamino]-penicillanic acid dihydrate (13.3 g.) in dimethylformamide (120 ml.) was added sodium carbonate (3.7 g.). After stirring at room temperature for 10 minutes the desired compound crystallized. The crystals were filtered off and treated with abs. ethanol (110 ml.). Inorganic material was separated by filtration and ether (110 ml.) was added to the filtrate whereupon the desired sodium salt crystallized. The crystals were filtered off and used in the next step without further purification.

Chloromethyl benzylpenicillinate

To a suspension of triethylammonium benzylpenicillinate (44 g) in dimethylformamide (400 ml) was added chloroiodomethane (40 ml).

After stirring overnight the mixture was diluted with ethyl acetate (1200 ml) and extracted with water (2×400 ml), 2% aqueous sodium bicarbonate (100 ml) and finally water (2×200 ml).

The organic phase was dried and evaporated in vacuo to yield chloromethyl benzylpenicillinate as a dark, viscous oil, which could be used in the next step without further purification.

A sample of the crude ester was purified by dry column chromatography on silica gel (Eluent:cyclohexaneethyl acetate 7:3) and the pure chloromethyl benzylpenicillinate thus obtained crystallized from ether:petroleum ether to yield colourless crystals with m.p. 92°–93° C.

$[\alpha]_D^{20}$ = +179.8° (c=1, CHCl$_3$).

The IR-spectrum (KBr) showed strong bands at: 1785, 1770, 1655, 1547, 1303, 1139, 1118 and 712 cm$^{-1}$.

The NMR-spectrum (CDCl$_3$) showed signals at $\delta$=1.51 (s), 3.64 (s), 4.41 (s), 5.53 (d, J=5), 5.68 (dd, J=5, J=9), 5.69 (d, J=6), 5.85 (d, J=6), 6.2 (d, J=8–9), and 7.35 8s) ppm. TMS was used as internal reference.

EXAMPLE 2

6-[(Hexahydro-1H-azepin-1-yl)-methyleneamino]-penicillanoyloxymethyl benzylpenicillinate, hydrochloride.

A solution of 6-[(hexahydro-1H-azepin-1-yl)-methyleneamino]-pencillanoyloxymethyl benzylpinicillinate in ethyl acetate was extracted with dilute hydrochloric acid (pH=2.5). The aqueous phase was separated and freeze-dried to afford the desired compound as a colourless amorphous powder.

EXAMPLE 3

6-[(Hexahydro-1H-azepin-1-yl)-methyleneamino]-penicillanoyloxymethyl phenoxymethylpenicillinate This compound was obtained as described in Example 1 by using chloromethyl phenoxymethylpenicillinate instead of chloromethyl benzylpinicillinate.

The NMR-spectrum (CDCl$_3$) showed peaks at $\delta$=1.51 (s), 1.53 (s), 1.60 (s), 1.67 (s), 1.6 (m), 3.38 (m), 4.41 (s), 4.50 (s), 4.58 (s), 5.11 (dd), 5.3–5.8 (m), 5.90 (s), 6.8–7.6 (m) and 7.65 (d) ppm. TMS was used as internal reference.

The IR-spectrum (CHCl$_3$) showed strong bands at 1768, 1685 and 1625 cm$^{-1}$.

Preparation of the starting material

Chloromethyl phenoxymethylpenicillinate

To a solution of phenoxymethylpenicillin (70 g) and triethylamine (29.4 ml) in dimethylformamide (250 ml) was added chloroiodomethane (80 ml), and the mixture was stirred for 3.5 hours at room temperature. Then the mixture was diluted with ethyl acetate (500 ml) and ether (500 ml), filtered, and the filtrate washed with water (3×250 ml), 0.5M aqueous sodium bicarbonate (100 ml), and water (2×100 ml). The organic phase was dried and evaporated in vacuo to yield the crude ester as a brownish gum, which could be used for the next step without further purification.

EXAMPLE 4

6-[(Hexahydro-1H-azepin-1-yl)-methyleneamino]-penicillanoyloxymethyl phenoxymethylpenicillinate, hydrochloride A solution of 6-[(hexahydro-1H-azepin-1-yl)-methyleneamino]-penicillanoyloxymethyl phenoxymethylpenicillinate in ethyl acetate was extracted with dilute hydrochloric acid (pH=2.5). The aqueous phase was freeze-dried to afford the desired compound as an amorphous powder.

EXAMPLE 5

Chloromethyl 6-[(hexahydro-1H-azepin-1-yl)-methyleneamino]-penicillanate

To a suspension of sodium 6-[(hexahydro-1H-azepin-1-yl)-methyleneamino]-penicillanate (0.5 g.) in dimethylformamide (5 ml) was added chloroiodomethane (1 ml). After stirring at room temperature for 3.5 hours the mixture was diluted with ethyl acetate (25 ml) and washed with water (3×5 ml).

The organic phase was extracted with dilute hydrochloric acid (pH~2.5). The aqueous phase was separated and made alkaline by adding sodium bicarbonate. The oil which separated was taken up in ethyl acetate and the solution was dried and evaporated to dryness in vacuo to yield the desired compound as a yellow oil.

The NMR-spectrum (CDCl$_3$) showed peaks at $\delta = 1.55$ (s), 1.68 (s), 1.62 (m), 3.45 (m), 4.42 (s), 4.20 (dd), 5.52 (d), 5.70 (d), 5.87 (d) and 7.66 (d) ppm. TMS was used as internal rereference.

EXAMPLE 6

6-[(Hexahydro-1H-azepin-1-yl)-methyleneamino]-penicillanoyloxymethyl benzylpenicillinate A solution of chloromethyl 6-[(hexahydro-1H-azepin-1-yl)-methyleneamino]-penicillanate (0.1 g) in dimethylformamide (2 ml) was stirred at room temperature with potassium benzylpenicillinate (0.1 g) for 65 hours. The mixture was diluted with ethyl acetate (8 ml) and washed with water (3×2 ml). The organic phase was dried and evaporated to dryness in vacuo to yield an amorphous powder. By thin layer chromatography on silica gel (Merck HF$_{254}$) in the following solvent systems the product had the following R$_f$-values:

I n-butanol-acetic acid—water (4:1:1): R$_f$=0.45.

II n-butanol-acetic acid—water (4:1:5) (upper layer): R$_f$=0.42.

III n-butyl acetate-n-butanol-acetic acid-methanol—1/15M phosphate buffer solution (pH=5.8) (80:15:40:5:24): R$_f$=0.27.

These R$_f$-values were identical to those of an authentic sample.

EXAMPLE 7

A. 6-Amino-penicillanoyloxymethyl benzylpenicillinate

To a suspension of potassium 6-amino-pencillanate (1.2 g) in dimethylformamide (20 ml) was added chloromethyl benzylpenicillinate (1.8 g). After stirring at room temperature for 48 hours the mixture was diluted with ethyl acetate (80 ml) and washed with water (3×10 ml). The organic phase was extracted with dilute hydrochloric acid (pH=2.5). The aqueous phase was made alkaline by adding sodium bicarbonate. The oil which separated was taken up in ethyl acetate. The solution was dried and evaporated to dryness in vacuo to yield the desired compound as an amorphous powder.

The NMR-spectrum (CDCl$_3$) showed peaks at $\delta = 1.45$ (s), 1/.50 (s), 1.63 (s), 2.25 (bs), 3.63 (s), 4.42 (s), 4.58 (d), 5.4–5.8 (m), 5.87 (s) and 7.33 (s) ppm. TMS was used as internal reference.

B. 6-[(Hexahydro-1H-azepin-1-yl)-methyleneamino]-penicillanoyloxymethyl benzylpenicillinate.

To N-formylhexamethyleneimine (1.3 g.) in dry ether (25 ml.) at 0°–5° was slowly added oxalyl chloride (0.85 ml.) in dry ether (5 ml.) with stirring. The mixture was stirred for 2½ hours at 0°–5°. The amide chloride formed was filtered off and washed with dry ether. It was kept in an desiccator.

The crude amide chloride (180 mg) in dry chloroform (3 ml) was slowly added to a solution of 6-aminopenicillanoyloxymethyl benzylpenicillinate (560 mg.) and triethylamine (0.28 ml.) in dry chloroform (3 ml.) at −40° with stirring. The yellow solution was stirred for half an hour at −20° whereupon the temperature was raised to 0° within 15 minutes. The solvent was removed in vacuo and the residue triturated with acetone (5 ml.). After filtration and evaporation in vacuo the oily residue was taken up in ether (25 ml.) and extracted with dilute hydrochloric acid (125 ml., pH~2.5). The aqueous phase was filtered and made alkaline (pH~7.5). The solid formed was filtered off and washed with water.

By thin layer chromatography in the solvent systems described in Example 6 of the product showed R$_f$-values identical to those of an authentic sample.

EXAMPLE 8

By following the procedure described in Example 1 and by replacing the chloromethyl benzylpenicillinate with the chloromethyl esters of 3-(2-chloro-6-fluorophenyl)-5-methyl-4-isoxazolylpenicillin and D(−)-α-azidobenzylpenicillin, respectively, the following compounds were prepared: 6-[(hexahydro-1H-azepin-1-yl)-methyleneamino]-penicillanoyloxymethyl 3-(2-chloro-6-fluorophenyl)-5-methyl-4-isoxazolylpenicillinate and 6-[(hexahydro-1H-azepin-1-yl)-methyleneamino]-penicillanoyloxymethyl D(−)-α-azidobenzylpenicillinate. The compounds were isolated as amorphous powders, the IR and NMR-spectra of which were as expected.

Preparation of the starting materials

The chloromethyl esters were prepared as described in Example 1 for chloromethyl benzylpenicillinate.

EXAMPLE 9

6-[(Hexahydro-1H-azepin-1-yl)-methyleneamino]-penicillanoyloxymethyl D(−)-α-aminobenzylpenicillinate, dihydrochloride A solution of 6-[(hexahydro-1H-azepin-1-yl)-methyleneamino]-penicillanoyloxymethyl D(−)-α-azidobenzylpenicillinate (5.1 g) in ethyl acetate (100 ml) was placed in a three-necked 500 ml flask equipped with a gas inlet-outlet tube, a glass-calomel combination electrode, a burette and a magnetic stirrer. Water (100 ml) was added and the system was flushed with nitrogen. 10% palladium-on-carbon catalyst (3 g) was added and a stream of hydrogen was bubbled through the suspension while stirring, a pH-value of 2.5 being maintained in the mixture by adding 1.0N hydrochloric acid. When the consumption of acid had ceased, the catalyst was filtered off. The aqueous phase was separated and freeze-dried to afford the desired compound as a colourless amorphous product The IR and NMR-spectra of this product confirmed that the reaction had taken place as expected.

EXAMPLE 10

6-[(N-ethyl-N-isopropylamino)-methyleneamino]-penicillanoyloxymethyl 3-(o-chlorophenyl)-5-methyl-4-isoxazolylpenicillinate Following the procedure described in Example 1 the above compound was prepared from sodium 6-[(N-ethyl-N-isopropylamino)-methyleneamino]-penicillinate and chloromethyl 3-(o-chlorophenyl)-5-methyl-4-isoxazolylpencillinate. The compound was isolated as an amorphous powder.

Preparation of the starting materials: Sodium 6-[(N-ethyl-N-isopropylamino)-methyleneamino]-penicillanate was prepared in analogy with sodium 6-[(Hexahydro-1H-azepin-1-yl)-methyleneamino]-penicillanate (vide Example 1).

Chloromethyl 3-(o-chlorophenyl)-5-methyl-4-isoxazolylpenicillinate was prepared in analogy with chloromethyl benzylpenicillinate (cfr. Example 1). The compound was isolated as an amorphous powder.

EXAMPLE 11

6-[(Hexahydro-1-(2H)-azocinnyl)-methyleneamino]-penicillanoyloxymethyl benzylpenicillinate This compound was prepared from sodium 6-[(hexahydro-1-(2H)-azocinnyl)-methyleneamino]-penicillanate and chloromethyl benzylpenicillinate following the procedure described in Example 1. It was obtained as an amorphous powder.

Preparation of the starting materials: Sodium 6-[(hexahydro-1-(2H)-azocinnyl)-methyleneamino]-penicillinate was prepared in analogy with sodium 6-[(hexahydro-1H-azepin-1-yl)-methyleneamino]-penicillinate (see Example 1).

In the claims, formula A is the following: A compound having the same formula as formula V but where X is H, and $R_1$ and $R_2$ represent an alkyl radical having from 1 to 6 carbon atoms, a cycloalkyl or cycloalkylalkyl radical the cycloalkyl part having from 3 to 10 carbon atoms, or $R_1$ and $R_2$ together with the nitrogen atom represent a heterocyclic ring with from 4 to 8 carbon atoms.

In the claims, formula B is the following: A compound having the same formula as formula II, but where X is H, and $R_3$ represents radicals known from natural, biosynthetic, and semisynthetic penicillins.

What is claimed is:

1. A method of treating bacterial infection in a warm blooded animal which comprises providing a 1:1 mixture of mecillinam and benzylpenicillin to the warm blooded animal.

* * * * *